United States Patent [19]

Mitani et al.

[11] Patent Number: 4,698,441
[45] Date of Patent: Oct. 6, 1987

[54] PROCESS FOR PRODUCING GLYOXYLIC ACID

[75] Inventors: Tadayuki Mitani; Mamoru Endo, both of Arai; Takashi Hiramoto, Fujimi, all of Japan

[73] Assignee: Daicel Chemical Industries, Ltd., Sakai, Japan

[21] Appl. No.: 439,505

[22] Filed: Nov. 5, 1982

[30] Foreign Application Priority Data

Nov. 16, 1981 [JP] Japan ............................. 56-183330

[51] Int. Cl.⁴ .......................................... C07C 51/235
[52] U.S. Cl. .................................................. 562/531
[58] Field of Search ........................................ 562/531

[56] References Cited

U.S. PATENT DOCUMENTS 3,281,466 10/1966 Gandon ............................... 562/531

FOREIGN PATENT DOCUMENTS 1002309 2/1957 Fed. Rep. of Germany ...... 562/531
103517 12/1973 Japan ................................... 562/531
129240 10/1980 Japan ................................... 562/531

Primary Examiner—Werren B. Lone
Attorney, Agent, or Firm—Flynn, Thiel, Boutell & Tanis

[57] ABSTRACT

A process for producing glyoxylic acid is disclosed which comprises oxidizing glyoxal with an aqueous oxidizing agent composition obtained from nitric acid and a nonoxidizing strong acid present in a concentration of 6 to 40 wt. % in the reaction mixture. Preferably, the nonoxidizing strong acid is hydrochloric acid and the reaction is carried out while nitric acid is gradually added to the reaction mixture so that the concentration of said nitric acid in said reaction mixture does not exceed 1 wt. % during the reaction.

9 Claims, 1 Drawing Figure

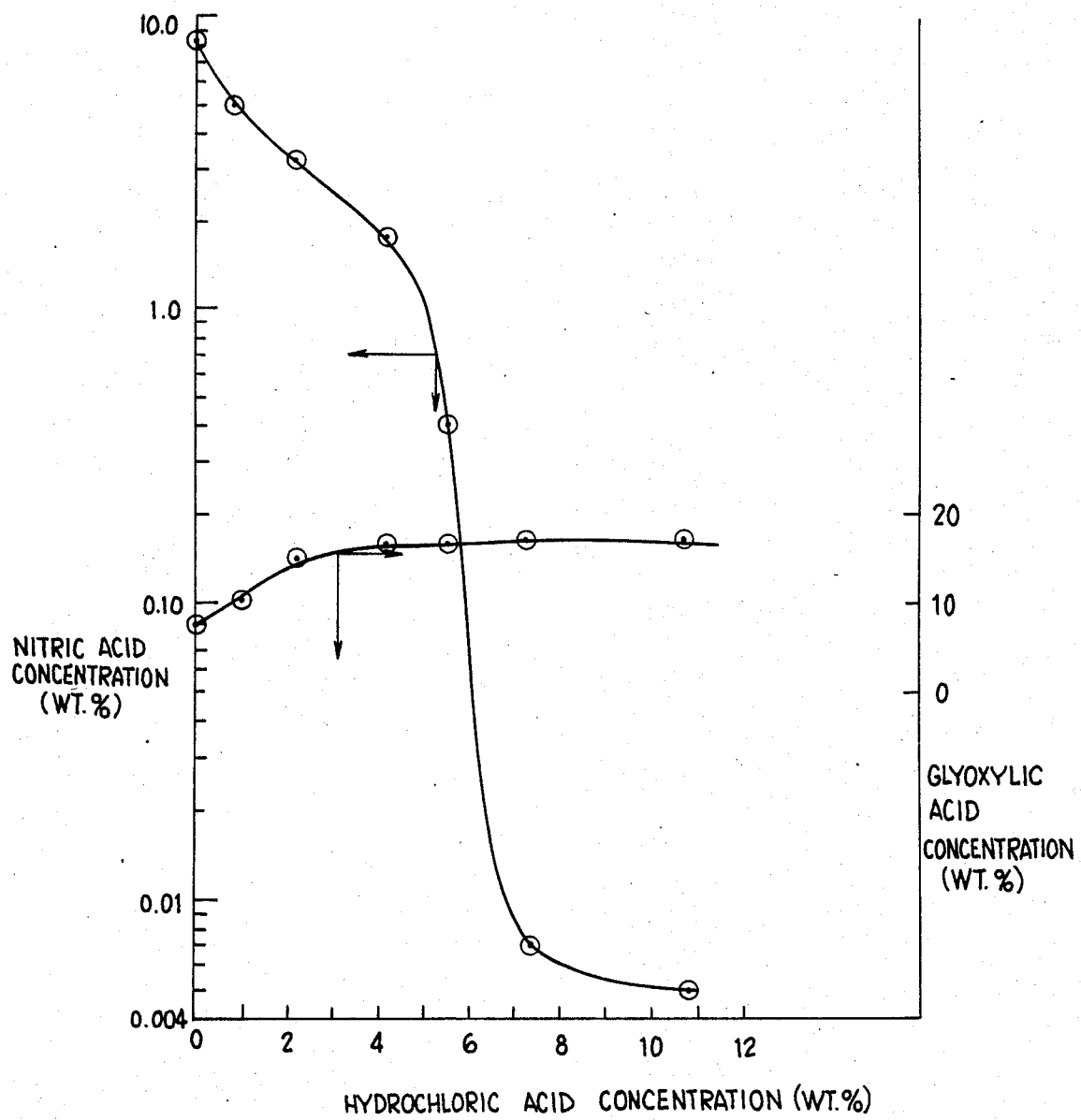

PROCESS FOR PRODUCING GLYOXYLIC ACID

This invention relates to a process for producing glyoxylic acid by oxidizing glyoxal in an aqueous solution.

It has long been known that the oxidation of glyoxal with dilute nitric acid gives glyoxylic acid. According to the process described in the specification of West German Pat. No. 932 369, a more highly concentrated aqueous solution of glyoxylic acid is obtained by the use of 30 to 50 wt. % nitric acid.

Nitric acid oxidation has been used as an industrial process for producing glyoxylic acid, but in such a process, in order to conduct the reaction smoothly and attain high conversion of glyoxal, nitric acid is conventionally used in an amount considerably exceeding the theoretical amount of 2/3 mole of nitric acid per mole of glyoxal. It is conventional that nitric acid is present in a concentration of about 5 wt. % or more in the reaction solution. For example, the nitric acid concentration in the solution is 5 to 7 wt. % in the process disclosed in Japanese Patent Laid-Open No. 29441/1976, and is 4 to 10 wt. % in the process disclosed in Japanese Patent Laid-Open No. 80821/1976. If the reaction in such processes is allowed to proceed after the addition of nitric acid has been completed, the concentration of nitric acid decreases somewhat, but the aqueous solution of glyoxylic acid obtained still contains at least 2 to 3 wt. % of nitric acid.

Generally, it is disadvantageous when nitric acid is present, as an impurity, in glyoxylic acid which is to be used as an organic synthesis material. A commercially acceptable aqueous solution of glyoxylic acid is usually required to have a nitric acid concentration of below 0.1 wt. %. Accordingly, aqueous solution of glyoxylic acid containing a considerable amount (2 to 5 wt. %) of nitric acid are not usable commercially, as such, and such solutions must be subjected to a refining process to remove the residual nitric acid, such as an ion exchange resin treatment or electrodialysis. However, these processes for removing residual nitric acid have the following drawbacks. The ion exchange resin treatment requires a high equipment cost and a large amount of ion exchange resin, and electrodialysis treatment requires an even higher equipment cost and has a refinement recovery of only 90 to 95%, which causes a considerable loss of glyoxylic acid.

Concerning other processes for the nitric acid oxidation of glyoxal, there have been proposed several improved processes, for example, a process including a step of supplying oxygen into the reaction system (Japanese Patent Laid-Open No. 80821/1976) and a process using an additive such as sulfuric acid (Japanese Patent Laid-Open No. 103517/1973). However, for these processes the situation is essentially the same in that a considerable amount of nitric acid remains in the reaction solution, and, in order to decrease the nitric acid concentration to below 0.1 wt. %, a step for removing nitric acid is required.

In view of these circumstances, the inventors have conducted research in order to find a process for producing glyoxylic acid which is capable of providing a reaction solution having a low residual nitric acid concentration. As a result, the inventors have discovered that by using nitric acid as a source material for forming an oxidizing agent, instead of reacting nitric acid directly with glyoxal, and by oxidizing the glyoxal with an aqueous oxidizing agent composition obtained by the interaction between the nitric acid and a nonoxidizing strong acid, which strong acid is present in the reaction solution in a concentration of 6 to 40 wt. %, an aqueous solution of glyoxylic acid having a residual nitric acid concentration of below 0.1 wt. % can readily be obtained. The present invention has been completed on the basis of these findings.

BRIEF DESCRIPTION OF THE DRAWING

The drawing is a graph showing the relationship between the hydrochloric acid concentration, on the one hand, and the nitric acid concentration and the glyoxylic acid concentration, on the other hand, of the reaction solution, according to the invention, as determined in the examples.

Among the aqueous oxidizing agent compositions usable in this invention, which compositions are obtained from nitric acid and a nonoxidizing strong acid having a concentration of 6 to 40 wt. %, some of such compositions are known. For example, a mixture of one volume of concentrated nitric acid and three volumes of concentrated hydrochloric acid is known as aqua regia. Aqua regia has a strong oxidizing and dissolving power because it contains nascent chlorine and nitrosyl chloride as shown in the reaction scheme (1):

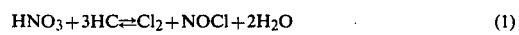

$$HNO_3 + 3HCl \rightleftharpoons Cl_2 + NOCl + 2H_2O \qquad (1)$$

In the present invention, in view of the need to maintain the nitric acid concentration at a low level, aqua regia itself, which contains nitric acid in a high concentration, is not desirable. Rather, it is preferred to use an aqueous oxidizing agent composition having the lowest possible nitric acid concentration and a relatively high hydrochloric acid concentration. More particularly, a composition having a hydrochloric acid concentration of from 6 to 40 wt. % and a nitric acid concentration of below 1 wt. % is preferred. A mixture having such an acid composition has an excellent oxidizing power, but because it is in a state of extreme dilution for use as an oxidizing agent, a large quantity thereof is required for effecting the oxidation of glyoxal, and such a large quantity is not suitable for use in a batch process. Accordingly, it is preferred, according to the invention, to carry out the oxidation by a semicontinuous process comprising starting the reaction using an oxidizing agent composition in an amount far less than the equivalent amount with respect to glyoxal, and supplementing the consumed oxidizing agent by sequentially adding additional nitric acid to the reaction mixture. In practice, this can be effected by gradually adding nitric acid to an aqueous reaction solution containing a large amount of hydrochloric acid.

More particularly, as nitric acid is added dropwise to a reaction solution containing hydrochloric acid in a high concentration and glyoxal, an oxidizing agent composition is formed in the system which immediately oxidizes the glyoxal to form glyoxylic acid. An amount of the oxidizing agent sufficient to compensate for the oxidizing agent consumed by this reaction is then generated from the hydrochloric acid already present in a large quantity in the system and the newly added nitric acid. Because the large quantity of hydrochloric acid already present in the system immediately converts newly added nitric acid into the above-mentioned oxidizing agent composition, nitric acid never accumulates in the system in a concentration exceeding 1 wt. %.

Even when the newly added nitric acid has a concentration as high as the solutions used in prior art processes, for example, 40 to 50 wt. % nitric acid, the concentration of nitric acid in the reaction solution usually remains at 0.1 wt. % or below in the invention process. About one hour after completing the addition of the nitric acid, an aqueous solution of glyoxylic acid having a residual nitric acid concentration of 0.1 wt. % or below can be obtained without need for a step of aging the solution by heating. In the invention process, the hydrochloric acid concentration must remain greater than 6 wt. %. The drawing shows that for HCl concentrations of less than 6 wt. %, the low hydrochloric acid concentration causes the residual nitric acid concentration to increase to unacceptably high levels.

According to the present invention, the oxidation reaction for forming glyoxylic acid can be carried out at a low nitric acid concentration in the reaction solution, i.e., the nitric acid concentration is on the order of at most one-tenth (1/10), at the completion of the nitric acid addition, or even one one-thousandth (1/1000), after completion of aging, compared to the typical residual nitric acid concentration of a conventional nitric acid oxidation, such as 5 wt. %.

Although the effectiveness of the invention process has been described with reference to the case wherein the nonoxidizing strong acid (HX) is hydrochloric acid (X=Cl), other nonoxidizing strong acids can be similarly used, namely, strong acids (pKa<O), which are completely dissociated when present in a concentration of 6 to 40 wt. % in aqueous solution, such as hydrobromic acid, dilute sulfuric acid and toluenesulfonic acid, and which do not oxidize glyoxal, that is, nonoxidizing strong acids different from acids which oxidize glyoxal, such as perchloric acid. Concentrated sulfuric acid oxidizes glyoxal, but dilute sulfuric acid used in the invention in a concentration of 6 to 40 wt. % in an aqueous reaction solution is nonoxidizing to glyoxal. Weak acids, such as acetic acid, cannot be used in the invention, and even moderately strong acids, such as phosphoric acid, when used in concentrations of about 15 wt. %, are not effective to decrease the nitric acid concentration of the reaction solution to the required low level.

Strong acids, such as hydrochloric acid and dilute sulfuric acid, when used in concentrations below about 6 wt. %, such as 3 wt. %, do not exhibit this effect of decreasing the nitric acid concentration. The effect of decreasing the nitric acid concentration of the reaction solution to 1 wt. % or lower and obtaining an aqueous solution of glyoxylic acid having a final residual nitric acid concentration of 0.1 wt. % or below can be obtained only when a monoxidizing strong acid is present in the reaction mixture in a concentration higher than a certain amount. This critical concentration can be determined from data shown in FIG. 1, for HCl, obtained by experiments. When the nonoxidizing strong acid is hydrochloric acid, the critical lower limit concentration is 6 wt. %, at a reaction temperature of 40° C., and preferably concentrations in the range of 7 to 20 wt. % are employed.

As shown in Example 4, a sulfuric acid concentration of about 14 wt. % proved to be a concentration higher than the critical lower limit concentration. It is expected that, at higher reaction temperatures, the critical lower limit of the concentration of the nonoxidizing strong acid will be reduced slightly but, judging from the fact that about 3 wt. % of nitric acid remains when the reaction solution is aged at 80° C. in the presence of about 3 wt. % of sulfuric acid, so that the desired low final nitric acid concentration cannot be obtained, it is estimated that, at high temperatures, the critical lower limit concentration of the nonoxidizing strong acid lies in a range of not much lower than 6 wt. %. On the other hand, the use of an excessively high concentration of the nonoxidizing strong acid is not economical, so that the concentration is usually 40 wt. % or less. Sulfuric acid has the disadvantage of exhibiting oxidizing effect on glyoxal at high concentrations. Accordingly, concentrations of 40 wt. % or less are suitable for the purposes of this invention.

Of the nonoxidizing strong acids set forth above, hydrochloric acid is the most suitable because it is readily available, for example, in large amounts as a by-product of organic chlorination reactions, it has the effect of improving the selectivity of the reaction for obtaining glyoxylic acid, and when removal of the nonoxidizing strong acid is required, an evaporation method can be used.

Glyoxal is usually available in hydrated form in an aqueous solution, and, in the present invention, glyoxal is used in the form of an aqueous solution thereof containing preferably 5 to 40 wt. % of glyoxal, especially 5 to 30 wt. % thereof. Commercially available refined aqueous solutions of glyoxal can be used. Lower-grade aqueous solutions of glyoxal can also be used. For example, even when an aqueous solution of glyoxal containing a large amount of glyoxylic acid, produced as a by-product in the production of glyoxal, is used, glyoxylic acid can be obtained in high yields without the disadvantages encountered when such an impure glyoxal solution is used as the starting material in a conventional nitric acid oxidation process, such as accumulation of nitric acid, poor reaction control, loss of selectivity, and the like.

With respect to the nitric acid, the quality, concentration and method of addition thereof can be similar to those used in conventional nitric acid oxidation processes. For example, the reaction is carried out by gradually adding technical grade nitric acid having a concentration of about 45 wt. % to the reaction solution. The oxidizing power of the nitric acid is transferred to the aqueous oxidizing agent composition obtained by the interaction of the nitric acid with the aqueous solution of the nonoxidizing strong acid, and the glyoxal is immediately oxidized. Nitrogen oxides, corresponding to the consumed nitric acid, become present in the vapor portion of the reactor and are removed therefrom in the form of an off-gas. These nitrogen oxides in the off-gas can be recovered as nitric acid by a known method, such as air oxidation followed by passing same through a water absorbing tower.

The reaction is carried out at the most desirable temperature, typically 20° to 70° C. If the concentration of the nonoxidizing strong acid is sufficient, the nitric acid concentration of the reaction solution can usually be maintained at 0.1 wt. % or lower when 50 wt. % nitric acid is gradually added (dropwise) to an aqueous solution of glyoxal. The total amount of nitric acid added can be a slight excess in relation to the theoretical amount ($\frac{2}{3}$ mole of nitric acid per mole of glyoxal). For example, 0.7 to 0.8 moles of nitric acid per one mole of glyoxal can be employed. When nitric acid is used in an excess amount, the nitric acid concentration of the reaction solution is increased slightly to about 0.5 wt. % at the end of the nitric acid addition, but the nitric acid concentration solution does not exceed 1 wt. %. The nitric acid concentration continues to decrease further after completion of the addition of nitric acid and usually reaches 0.005 to 0.03 wt. % in about one hour. Therefore, an aqueous solution of glyoxylic acid having a residual nitric acid concentration of 0.01 wt. % or below can be obtained without purification. In conventional nitric acid oxidation processes, the conversion of glyoxal is scarcely increased merely by adding nitric acid at about 40° C., even when the reaction is promoted by adding about 0.1 mole of sulfuric acid or hydrochloric acid, so that an aging step has generally been carried out by heating the reaction solution to about 80° C. after completion of the nitric acid addition. In this invention, by contrast, aging by heating is not necessary.

The drawing is a graph illustrating the relationship between the hydrochloric acid concentration, on the one hand, and the nitric acid concentration and the glyoxylic acid concentration, on the other hand, of the reaction solution obtained by gradually adding 154 g of 45 wt. % nitric acid to 435 g of an aqueous solution containing glyoxal at a starting concentration of 20 wt. % and hydrochloric acid at a starting concentration of from 0 to 15 wt. % over a period of four hours, at a reaction temperature of 40° C., and then aging that reaction mixture at the same temperature for one hour after completion of nitric acid addition. This graph shows that when the oxidation reaction of glyoxal is conducted in a relatively large amount of hydrochloric acid, the residual nitric acid concentration decreases to about one one-hundredth (1/100) of that in the case in which the hydrochloric acid concentration is smaller than 6±1%, and various kinds of reaction proceed around the critical hydrochloric acid concentration of 6±1%. In other words, when the hydrochloric acid concentration is smaller than the critical value, the oxidation reaction appears to proceed substantially by nitric acid, though hydrochloric acid provides the promoting effect. Contrary to that, when the hydrochloric acid concentration is larger than the critical value, 6%, an aqueous oxidizing agent composition is formed from nitric acid and hydrochloric acid so that the oxidation reaction of glyoxal can take place even while the nitric acid concentration is too small to oxidize glyoxal by itself.

A difference between the invention and the prior arts appears in the off gas of the process. In the prior arts, the gas phase looks black due to a large amount of $NO_2$ gas. On the other hand, the gas phase of the process according to the invention looks clear because $NO_2$ gas is hardly produced. Also an $N_2O$ content in the off gas is remarkably reduced in the invention, while it is 20 to 30% in the prior processes.

If nitric acid is added sequentially to an aqueous solution of glyoxal so that the nonoxidizing strong acid is kept at a concentration of 6 wt. % or higher in the reaction mixture, the reaction can proceed in a state wherein nitric acid is not present in the reaction solution in a concentration exceeding 1 wt. %, and an aqueous solution of glyoxylic acid having a final residual nitric acid concentration of 0.1 wt. % or below can be easily obtained. Thus, it is possible to omit the step of removing residual nitric acid, which step is conventionally required, and to use the aqueous solution of glyoxylic acid obtained by the process of the invention directly in further synthesis reactions.

In addition, when a glyoxylic acid solution not containing any residual strong acid is desired, such a solution can be obtained by subjecting an aqueous solution of glyoxylic acid obtained by the process of this invention to a treatment for removing the nonoxidizing strong acid, for example, evaporation of hydrochloric acid.

Most of the nitric acid used as an oxidizing agent in a glyoxal oxidation process can be recovered from the nitrogen oxides in the by-product gas. Thus, the nitric acid that is industrially unrecoverable and is lost is mainly the residual nitric acid present in the reaction solution after the reaction is completed. It is disadvantageous in the prior arts that $N_2O$ appears in the off gas, which cannot be recovered as nitric acid and so is lost. Accordingly to the invention, the residual nitric acid concentration is very small in the reaction mixture and only a very small amount of $N_2O$ appears in the off gas. Thus almost all nitrogen oxides are found to be NO in the invention. For this reason nitric acid can be recovered in a high efficiency in the invention. It results from the fact that an amount of nitric acid to be added in the invention is smaller by about one seventh or less than that required in the prior arts. This is advantageous from the economic point of view. Furthermore, because the problem of nitric acid accumulation that is frequently encountered in conventional nitric acid oxidation processes does not occur in the invention process, neither an uncontrollable reaction nor a rapid discharge of a large quantity of $NO_x$-containing by-product gas occurs. Thus, the present invention is also extremely advantageous from the standpoint of controlling the operation of the process and preserving the environment.

Moreover, when hydrochloric acid is used as the nonoxidizing strong acid, the selectivity of the reaction for producing glyoxylic acid is improved as compared with conventional nitric acid oxidation processes.

This invention will now be described in further detail with reference to the following illustrative examples and comparative examples. In the examples, percent amounts are by weight unless stated otherwise.

EXAMPLE 1

An aqueous oxidizing agent composition was continuously formed and, at the same time, glyoxal was oxidized by heating 397.5 g of an aqueous solution containing 14.75% of glyoxal, 1.52% of glyoxylic acid and 15.01% of hydrochloric acid to 60° C., and gradually adding 111.4 g of 40.0% nitric acid to the solution at 60° C. over 2.5 hours. After completion of the nitric acid addition, the reaction solution was agitated at 60° C. for one hour to obtain 857.7 g of an aqueous solution of glyoxylic acid (13.45%) having a residual nitric acid concentration of 0.02%. The other principal components contained in the solution were hydrochloric acid (12.03%), oxalic acid (2.03%) and glyoxal (1.11%). The conversion of glyoxal was 90.8%, the selectively was 87.3% and the yield, based on the glyoxylic compounds (glyoxal plus glyoxylic acid), was 80.8%. 0.49 moles of nitric acid were recovered from the off-gas by means of air oxidation and a water absorbing tower.

EXAMPLE 2

154 g of 45% nitric acid was added dropwise to 435 g of an aqueous solution containing 19.96% of glyoxal, 0.49% of glyoxylic acid and 10.02% of hydrochloric acid, at a temperature of 40° C., over four hours, whereby glyoxal was oxidized at 40° C. with an oxidizing agent composition formed in situ. After one hour, at the same temperature, from the completion of the addition of nitric acid, a reaction solution containing 16.58% of glyoxylic acid and 0.007% of nitric acid was obtained. This reaction solution also contained 0.84% of glyoxal, 7.34% of hydrochloric acid and 3.31% of oxalic acid. The conversion of glyoxal was 94.7%, the selectivity for glyoxylic acid was 84.7% and the yield was 82.1%.

EXAMPLE 3

Glyoxal was oxidized at 40° C. in essentially the same manner as described in Example 2, except that the initial hydrochloric acid concentration was 14.89%. One hour after the completion of the addition of nitric acid, an aqueous solution of glyoxylic acid (16.07%) having a residual nitric acid concentration of 0.005% was obtained. The final concentration of hydrochloric acid was 10.81%, and the yield of glyoxylic acid was 81.8% (selectivity 86.9%).

Additional reactions were carried out under the same conditions, except that a variety of different hydrochloric acid concentrations were used. The obtained results are shown in Table 1, and the relationship between the hydrochloric acid concentration and the nitric acid concentration and glyoxylic acid concentration of the reaction solution is shown in the drawing.

TABLE

|  | Composition of Reaction Solution | | | Results of Reaction | |
| --- | --- | --- | --- | --- | --- |
|  | HCl (%) | HNO$_3$ (%) | Glyoxylic Acid (%) | Conversion (%) | Selectivity (%) |
| Example 3 | 10.81 | 0.005 | 16.17 | 92.8 | 86.9 |
| Example 2 | 7.34 | 0.007 | 16.58 | 94.7 | 84.7 |
| Comparison | 5.59 | 0.40 | 15.86 | 95.1 | 81.9 |
| Comparison | 4.27 | 1.79 | 15.91 | 89.4 | 89.0 |
| Comparison | 2.29 | 3.25 | 14.16 | 78.5 | 88.8 |
| Comparison | 0.93 | 5.02 | 10.09 | 60.7 | 82.4 |
| Comparison | 0 | 8.37 | 8.34 | 39.9 | about 100 |

EXTAMPLE 4

Glyoxal was oxidized in essentially the same manner as described in Examples 2 and 3 except that, instead of using hydrochloric acid, an aqueous solution containing sulfuric acid (initial concentration 14.16%) was used and the reaction temperature was 60° C. After one hour at 60° C. from the completion of the nitric acid addition, an aqueous solution of glyoxylic acid (13.57%) having a nitric acid concentration of 0.011% was obtained. The conversion of glyoxal was 97.5%, and the selectivity for glyoxylic acid was 66.8%.

COMPARATIVE EXAMPLE 1

Glyoxal was oxidized in essentially the same manner as described in Example 4 except that, instead of using sulfuric acid, an aqueous phosphoric acid solution having an initial concentration of 15.05% was used. After one hour at 60° C. from the completion of the nitric acid addition, an aqueous solution of glyoxylic acid (11.74%) was obtained, but this solution contained 3.04% of nitric acid.

Another reaction was conducted in the same way, except that aluminum nitrate of an initial concentration of 27.6% (calculated as Al(NO$_3$)$_3$.9H$_2$O) was used in place of phosphoric acid, at a reaction temperature of 40° C. The obtained aqueous solution contained 10.67% glyoxylic acid and it had a nitric acid concentration of 7.61%. Thus, additives other than a nonoxidizing strong acid, even in large amounts, are not effective to obtain glyoxylic acid products having low nitric acid concentrations as in the present invention.

COMPARATIVE EXAMPLE 2

Glyoxal was oxidized at 40° C. in the same manner as described in Example 3 except that hydrochloric acid having an initial concentration of 1.20% (0.1 moles per mole of glyoxal) was used. As a result, after one hour from the completion of the nitric acid addition, the reaction solution contained 5.02% of nitric acid and 5.91% of glyoxal. The conversion of glyoxal was only 60.7%.

Thus, the use of hydrochloric acid in an amount as small as that taught in Japanese Patent Laid-Open No. 103517/1973, namely, 0.02-0.2 moles per mole of glyoxal, or about 0.2-2% in terms of the concentration of hydrochloric acid in the reaction solution, is not adequate unless high-temperature aging is carried out because the conversion obtained by such a process is extremely low.

COMPARATIVE EXAMPLE 3

177 g of 45% nitric acid was added dropwise to 435 g of an aqueous solution containing sulfuric acid in an initial concentration of 3.19% and glyoxal in an initial concentration of 20%, at 40° C., over four hours, and thereafter the reaction solution was heated to 80° C. and aged for one hour. The produced aqueous solution of glyoxylic acid (13.14%) had a residual nitric acid concentration of 2.06%. The conversion was 90.9% and the selectivity was 74.2%.

The residual nitric acid concentration was 3.24% when a similar oxidation reaction was carried out under the same reaction conditions except that phosphoric acid having an initial concentration of 4.21% was used instead of sulfuric acid. Further, the residual nitric acid concentration was 3.24% when aluminum nitrate having an initial concentration of 2.53% was used under conditions otherwise identical to the above. Consequently, as indicated by the prior art, it was confirmed that when an added acid, whether a strong acid or not, is used in a small amount, about 2 to 3% nitric acid remains in the reaction solution obtained after high-temperature aging, which result is not essentially different from that observed in the conventional nitric acid oxidation process.

The embodiments of the invention in which an exclusive property or privilege is claimed are defined as follows:

1. A process for preparing an aqueous solution of glyoxylic acid containing less than 0.1 wt. % of nitric acid, which comprises:

forming an aqueous liquid reaction solution of glyoxal and containing dissolved therein from 6 to 40 wt. % of a nonoxidizing strong acid having a pKa <0 and selected from the group consisting of hydrochloric acid, hydrobromic acid, sulfuric acid and toluene sulfonic acid, which acid is completely dissociated in said solution and which acid does not oxidize said glyoxal in said solution; and adding nitric acid to said reaction solution in incremental amounts so that the concentration of said nitric acid in said reaction solution does not exceed 1 wt. %, whereby said nitric acid reacts with said nonoxidizing strong acid to form, in situ in said aqueous solution, an oxidizing agent which oxidizes said glyoxal to glyoxylic acid.

2. A process according to claim 1, wherein the concentration of said strong acid in said reaction solution is 7 to 20 wt. %.

3. A process according to claim 1, wherein said nonoxidizing strong acid is hydrochloric acid.

4. A process according to claim 1, wherein said glyoxal is present in said aqueous reaction solution in an initial concentration in the range of 5 to 40 wt. % and the reaction temperature is from 20° to 70° C.

5. A process according to claim 4, wherein the nitric acid added to said solution is aqueous nitric acid containing 40 to 50 wt. % of nitric acid, and the total amount of said nitric acid added is in the range of approximately 2/3 to 0.8 mole of nitric acid per one mole of said glyoxal.

6. A process according to claim 1, including the further step of allowing said reaction solution to stand at least one hour after completion of the addition of said nitric acid.

7. A process for preparing an aqueous solution of glyoxylic acid containing less than 0.1 wt. % of nitric acid, consisting essentially of the steps of:
(A) forming an aqueous liquid reaction solution comprising 5 to 40 wt. % glyoxal, 6 to 40 wt. % of a strong acid selected from the group consisting of hydrochloric acid, hydrobromic acid, sulfuric acid and toluene sulfonic acid, which strong acid is completely dissociated in said solution and which acid does not oxidize said glyoxal in said solution, and the balance is essentially water, said reaction solution being at a reaction temperature in the range of 20° C. to 70° C.;
(B) adding an aqueous nitric acid solution to said reaction solution gradually at said reaction temperature so that the concentration of nitric acid in said reaction solution never exceeds 1 wt. % and the total amount of nitric acid added is in the range of 2/3 to 0.8 mole of nitric acid per one mole of starting glyoxal; and
(C) allowing said reaction solution to stand for at least 1 hour to thereby obtain a product solution consisting essentially of glyoxylic acid, said strong acid, oxalic acid, glyoxal, less than 0.1 wt. % of nitric acid as an impurity, and the balance is essentially water.

8. A process for preparing an aqueous solution of glyoxylic acid containing less than 0.1 wt. % of nitric acid, consisting essentially of the steps of:
(A) forming an aqueous liquid reaction solution comprising 5 to 40 wt. % glyoxal, glyoxylic acid produced as a by-product in the production of said glyoxal, 6 to 40 wt. % of a strong acid selected from the group consisting of hydrochloric acid, hydrobomic acid, sulfuric acid and toluene sulfonic acid, which strong acid is completely dissociated in said solution and which acid does not oxidize said glyoxal in said solution, and the balance is essentially water, said reaction solution being at a reaction temperature in the range of 20° C. to 70° C.;
(B) adding an aqueous nitric acid solution to said reaction solution gradually at said reaction temperature so that the concentration of nitric acid in said reaction solution never exceeds 1 wt. % and the total amount of nitric acid added is in the range of 2/3 to 0.8 mole of nitric acid per one mole of starting glyoxal; and
(C) allowing said reaction solution to stand for at least one hour to thereby obtain a product solution consisting essentially of glyoxylic acid, said strong acid, oxalic acid, glyoxal, less than 0.1 wt. % of nitric acid as an impurity, and the balance is essentially water.

9. A process as claimed in claim 8, wherein said reaction solution in step (A) contains 5 to 30 wt. % glyoxal and 7 to 20 wt. % of said strong acid.

* * * * *